United States Patent
Wieres et al.

(10) Patent No.: US 6,510,239 B1
(45) Date of Patent: Jan. 21, 2003

(54) METHOD AND APPARATUS FOR DETERMINING A CELL DENSITY OF A HONEYCOMB BODY, IN PARTICULAR FOR AN EXHAUST GAS CATALYTIC CONVERTER

(75) Inventors: Ludwig Wieres, Overath (DE); Abderrahim Aouab, Hamburg (DE)

(73) Assignee: EMITEC Gesellschaft fuer Emissionstechnologie mbH, Lohmar (DE)

( * ) Notice: Subject to any disclaimer, the term of this patent is extended or adjusted under 35 U.S.C. 154(b) by 0 days.

(21) Appl. No.: 09/316,477

(22) Filed: May 21, 1999

Related U.S. Application Data

(63) Continuation of application No. PCT/EP97/06349, filed on Nov. 13, 1997.

(30) Foreign Application Priority Data

Nov. 21, 1996 (DE) .......................... 196 48 272

(51) Int. Cl.⁷ .................................................. G06K 9/60
(52) U.S. Cl. ................... 382/141; 356/397; 250/559.24
(58) Field of Search ................................. 382/108, 133, 382/141, 152; 356/628, 397, 237.1; 502/527.19, 527.2, 527.21, 527.22; 250/559.2, 559.24, 559.39, 559.46; 348/92, 93, 129, 136, 137; 428/593, 72, 73, 116–118, 314.8; 228/181, 157; 493/966; 359/894

(56) References Cited

U.S. PATENT DOCUMENTS

| | | | | |
|---|---|---|---|---|
| 4,319,840 A | | 3/1982 | Kondo et al. | ............... 356/241 |
| 4,340,281 A | * | 7/1982 | McIntyre | ........................ 351/6 |
| 4,557,773 A | | 12/1985 | Bonzo | .......................... 156/64 |
| 4,845,558 A | | 7/1989 | Tsai et al. | .................... 358/106 |
| 4,975,972 A | | 12/1990 | Bose et al. | ..................... 382/8 |
| 5,181,255 A | * | 1/1993 | Bloomberg | .................... 382/9 |
| 5,212,637 A | * | 5/1993 | Saxena | .................. 364/413.26 |
| 5,331,472 A | * | 7/1994 | Rassman | .................... 359/894 |
| 5,433,904 A | | 7/1995 | Noky | ........................ 264/40.1 |
| 5,463,462 A | * | 10/1995 | Ohnishi et al. | ............. 356/354 |
| 5,621,488 A | * | 4/1997 | Hanamura et al. | .......... 351/206 |

FOREIGN PATENT DOCUMENTS

| | | | | |
|---|---|---|---|---|
| EP | 0 400 777 A2 | 12/1990 | .......... | G01N/21/88 |
| EP | 0 599 081 B1 | 6/1994 | .......... | G01N/21/88 |
| EP | 0 599 081 A2 | 6/1994 | .......... | G01N/21/88 |
| JP | 4-69553 A | * 3/1992 | .......... | G01N/21/84 |

\* cited by examiner

*Primary Examiner*—Brian Werner
(74) *Attorney, Agent, or Firm*—Laurence A. Greenberg; Werner H. Stemer; Ralph E. Locher

(57) ABSTRACT

A method and an apparatus are provided for automatically determining an area-related cell density of a cell structure of a honeycomb body having a plurality of passages that are open-ended at an end of the honeycomb body at which the cell structure is visible. An image which has a known or ascertainable image scale of at least a portion of the cell structure is recorded with an optical instrument and the image is processed. In the image processing operation the number of cells is established by counting cells and the cell density is calculated by relating the number of cells to a reference area established through the use of the image scale. The cell density can be rapidly and accurately determined in such a way particularly when using computer-aided image processing. Therefore, production errors can be quickly detected and costs can be saved in that manner.

25 Claims, 1 Drawing Sheet

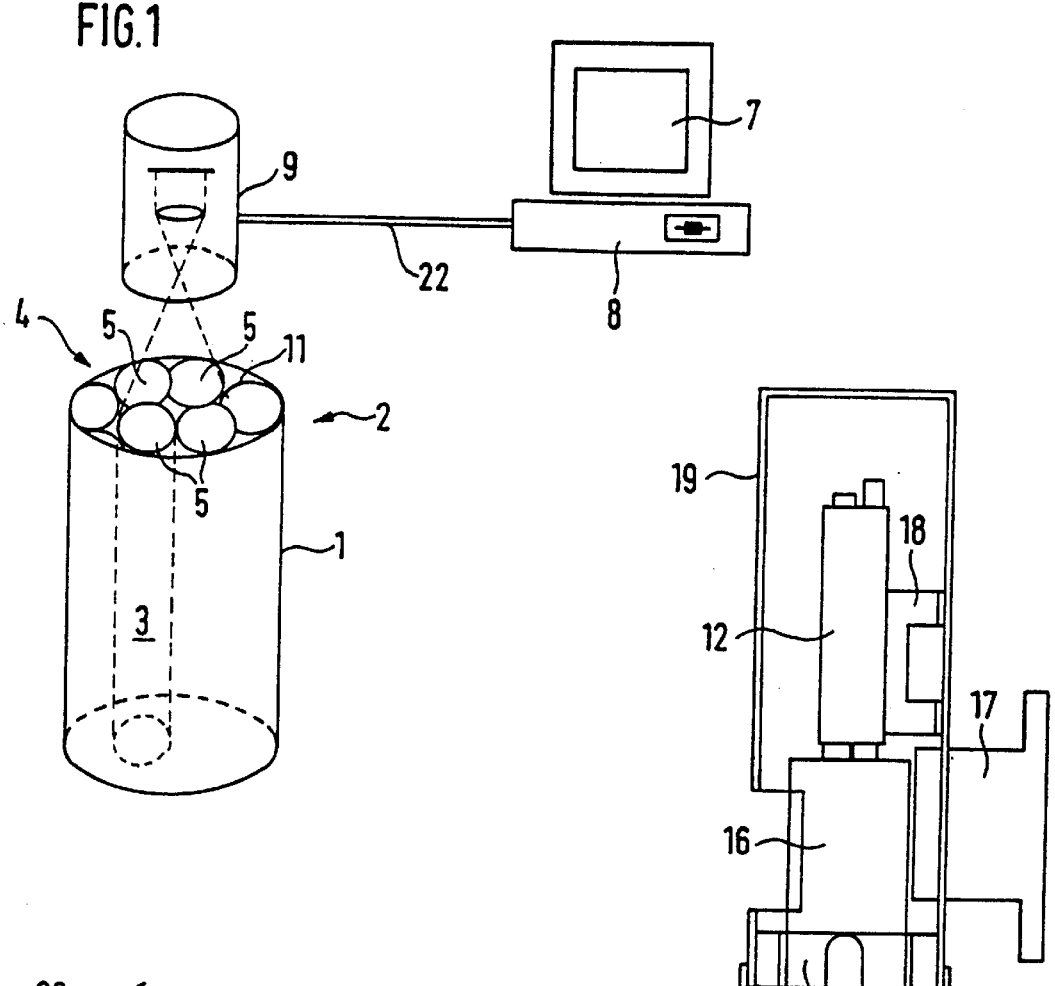
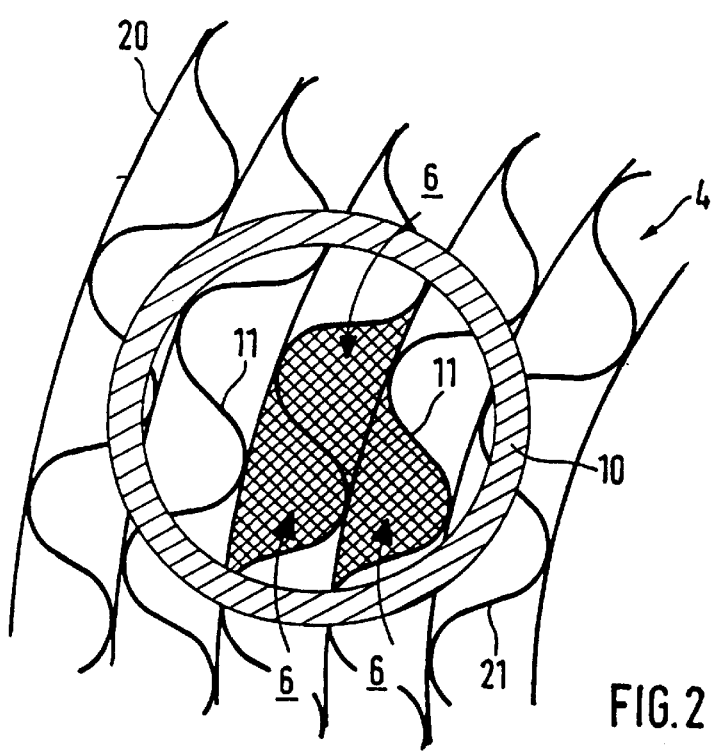

METHOD AND APPARATUS FOR DETERMINING A CELL DENSITY OF A HONEYCOMB BODY, IN PARTICULAR FOR AN EXHAUST GAS CATALYTIC CONVERTER

CROSS-REFERENCE TO RELATED APPLICATION

This application is a continuation of copending International application No. PCT/EP97/06349, filed Nov. 13, 1997, which designated the United States, and was published on May 28, 1998 under International Publication No. WO 98/22796.

BACKGROUND OF THE INVENTION

Field of the Invention

The present invention relates to a method and an apparatus for determining an area-related cell density of a cell structure of a honeycomb body having a plurality of passages which are open-ended at an end of the honeycomb body. Such honeycomb bodies are used in particular as carrier bodies for exhaust gas catalysts which permit catalytic conversion of exhaust gases from an internal combustion engine. The area-related cell density is an essential parameter of such honeycomb bodies. The cell density is usually related to the cross-sectional area or a part thereof, that is to say it is transverse relative to a flow direction that is predetermined by the passages. The usual unit is cells per square inch, cpsi. The area-related cell density is established in the mass production of the honeycomb bodies. In the case of extruded honeycomb bodies, it is possible for the area-related cell density to be definitively established through the use of a negative mould with which the honeycomb bodies are produced in series manufacture. However, especially in the production of honeycomb bodies being formed of sheet metal layers, the area-related cell density changes during the manufacturing procedure, with its final value depending on the management of the manufacturing procedure. For that reason, continuous monitoring and possibly regulation of the manufacturing procedure by checking the area-related cell density is required, at least on a random sample basis. One way is to select individual finished honeycomb bodies and to determine the number of cells thereof by counting them out by hand. The area-related cell density is obtained by relating the number of cells to a previously known or measured reference area, for example a cross-sectional area of a tubular casing of a honeycomb body. The operation of counting the number of cells by hand is time-consuming and susceptible to error. The person who is carrying out the checking operation can easily miscount and the reference area is under some circumstances not precisely known or is incorrectly measured. With a cell density of 600 cpsi, for example, it is only possible for a substantially smaller cross-sectional area than 1 square inch to be counted out, at reasonable cost.

SUMMARY OF THE INVENTION

It is accordingly an object of the invention to provide a method and an apparatus for determining an area-related cell density of a honeycomb body, in particular for an exhaust gas catalytic converter, which overcome the hereinafore-mentioned disadvantages of the heretofore-known methods and apparatuses of this general type and which permit automatable, rapid, inexpensive and precise determination.

With the foregoing and other objects in view there is provided, in accordance with the invention, a method of automatically determining an area-related cell density of a cell structure of a honeycomb body including a multiplicity of passages having open ends at an end of the honeycomb body at which the cell structure is visible, the method which comprises recording an image having a known or ascertainable image scale of at least a portion of the cell structure, with an optical instrument; and processing the image by establishing a number of cells by counting cells and calculating the cell density by relating the number of cells to a reference area established with the aid of the image scale.

The number of cells is counted and the cell density is calculated by relating the number of cells to a reference area, as in the case of the above-described manual method, but according to the invention it is done automatically. Use is made of the image scale, in the operation of establishing the reference area. The automatic determination procedure can be carried out quickly and reliably and saves on labor costs. It is also possible to increase the percentage of random samples or to check all honeycomb bodies produced in a manufacturing procedure, in regard to their area-related cell density, at a low level of additional expenditure. The method can be integrated directly into the manufacturing procedure or it can be performed in a separate method step. Due to its rapidity, it is possible in both cases to correct the manufacturing procedure without delay in order to abide by the predetermined parameters, in the event of an area-related cell density that deviates from predetermined parameters. It is therefore possible to avoid whole series of honeycomb bodies from failing to correspond to the predetermined parameters.

If it is not the entire cell structure of a honeycomb body but only a part of such a structure that is evaluated, it is possible for incomplete images of cells to be produced. Therefore, in accordance with another mode of the invention, only cells with respect to which complete images are produced are counted and cell cross-sectional areas of the individual cells are established through the use of the image scale. The sum of the individual cell cross-sectional areas is equal to the reference area. That procedure makes it possible to achieve a high degree of precision in determining the area-related cell density since estimating errors when estimating the size of a cell with respect to which an incomplete image has been produced are not involved.

In accordance with a further mode of the invention, the counted cells form a coherent region of the cell structure. An advantage of this is that the optical instrument and the honeycomb body can be put into a fixed position relative to each other which then no longer needs to be altered.

In accordance with an added mode of the invention, an area average of the cell cross-sectional areas is calculated, an area tolerance range is ascertained and, if the cell cross-sectional area of a cell falls below the area tolerance range, the cell is not included in the count when calculating the number of cells. In that way errors can be corrected, in terms of recognition of cells. It can be assumed in many cases that the cell cross-sectional areas are almost all approximately equal. If the cell cross-sectional area of a cell falls below the area tolerance range, it is then assumed that a cell wall which was not present was wrongly involved when processing the image and/or when recording the image.

In accordance with an additional mode of the invention, an area average of the cell cross-sectional areas is calculated, an area tolerance range is ascertained and, if the cell cross-sectional area of a cell exceeds the area tolerance range, the cell is counted two or more times in the operation of counting the number of cells. The determination as to how many times it contributes to the number of cells depends on how many times larger the cell cross-sectional area of the cell is than the area average. In that way errors due to non-recognized cell walls can be corrected. Particularly in the case of honeycomb bodies with mutually adjoining smooth and corrugated sheet layers, there may be individual, incompletely bordered cells which can be treated as completely bordered cells, with this development of the method. That is desirable since a narrow communicating opening between two cells is of only slight practical significance. Checks concerning the method have shown that, with a suitable selection with respect to the area tolerance range, the area-related cell density can be determined with a relative error of 0.5%.

As mentioned above, the image has a known or ascertainable image scale. In accordance with yet another mode of the invention, it is desirable if a scale object which is of known dimensions is immovably mounted, preferably glued, to the end of the honeycomb body, and if the scale object is at least partially also recorded in the image, so that there exists a scale which is the image scale or with which the image scale is formed. When forming the image scale, it is possible to use additional items of information, for example a possibly known spacing from the optical instrument to the end of the honeycomb body. A scale object which is at least partially also recorded with the image and which is of known dimensions affords the advantage that distortion phenomena of the image, which can occur, for example, in the processing operation, can be corrected. It is particularly advantageous to use two mutually independent image scales for two orthogonal image axes of the image.

In accordance with yet a further mode of the invention, an extent of the scale object along the extent of the cell structure is substantially larger than its extent perpendicularly to the extent of the cell structure. On one hand, it is desirable if the extent of the scale object along the cell structure is great in order to achieve a scale error which is as slight as possible. On the other hand, parts of the cell structure which are beside the scale object should not be partially masked by large extents of the scale object perpendicularly to the extent of the cell structure since otherwise under some circumstances the image is defectively recorded and/or defectively processed.

In accordance with yet an added mode of the invention, the scale object is a frame, preferably a circular ring, which frames a region of cells. In that case, the framed region and at least the inner frame edge and preferably also the outer frame edge are completely recorded in the image and only cells out of the framed region are counted. The use of that procedure presupposes that the framed cells are of a size which is representative of all cells or that especially the framed cells are to be evaluated. It is desirable if the frame clearly stands out optically from the cell structure, for example by it having a surface which provides good light reflection. The inner and/or the outer frame edge serve to establish the image scale.

In accordance with yet an additional mode of the invention, the end of the honeycomb body is illuminated so that light is reflected from the cell edges in the direction of the optical instrument. The end, or the part thereof of which an image is to be produced, should be uniformly illuminated so as to ensure reliable recognition of the cell edges.

In accordance with again another mode of the invention, a brightness average is formed over at least a part of the image, a brightness threshold value which is above the brightness average is ascertained, and the position of the cell edges is inferred from the position of image regions having a brightness that is above the brightness threshold value. The brightness threshold value affords a reliable criterion in terms of recognizing the cell edges, provided that less light passes out of the cavities of the cells in the direction of the optical instrument than is reflected by the cell edges in that direction.

In accordance with again a further mode of the invention, the image is processed through the use of a computer program which acquires predeterminable parameter values, in particular a scale value, by virtue of suitable value allocations. That permits inexpensive and particularly rapid processing of the image.

Further useful developments of the invention are opened up by virtue of the use of a computer. Therefore, in accordance with again an added mode of the invention, a configuration of counted cells is represented in two-dimensional form, preferably on a display screen, as a result of image processing. A variant of this kind of representation is a representation by printing out on paper through the use of a computer-controlled printer. However, representation on a display screen is generally faster. It permits results of the image processing operation to be the subject of a visual display in clear form and enables the mode of operation of the method to be followed.

In accordance with again an additional mode of the invention, the configuration also includes uncounted cells and the counted cells are emphasized optically, preferably in color, relative to the uncounted cells. That considerably increases the degree of clarity.

With the objects of the invention in view, there is also provided an apparatus for automatically determining an area-related cell density of a cell structure of a honeycomb body, comprising a scale object having a known or ascertainable image scale for establishing a reference area, the scale object framing a region of cells at an end of a honeycomb body; an optical instrument having a matrix camera for recording an image of a honeycomb body; and a data processing installation for ascertaining a number of cells by counting cells and for determining a cell density by relating the ascertained number of cells to the reference area.

A system of digital pixels is associated with the cell structure, or a part thereof, through the use of the matrix camera. That affords all options in terms of computer-aided digital image processing.

In accordance with another feature of the invention, the image recording apparatus has an internal lamp, preferably a circular slit lamp, for illuminating the end of the honeycomb body, and a peripherally closed external light shielding device with an object opening. The internal lamp is disposed in such a way that when the internal lamp is switched on the light thereof passes outwardly out of the external light shielding device through the object opening. The object opening is preferably an opening with a flat edge. The cell structure, of which the image is to be produced, or a part thereof, can be entirely or partially shielded from external light through the use of the external light shielding device. That considerably facilitates image processing, with a known intensity of illumination of the internal lamp. Thus the image can be processed, for example, by using a previously ascertained brightness threshold value or grey threshold value.

In accordance with a further feature of the invention, the edge of the object opening, preferably in peripheral relationship, bears against the end of the honeycomb body.

In accordance with a concomitant feature of the invention, a computer-readable data carrier is provided with a computer program which is used to process the image in accordance with the described embodiments of the method of the invention. Such a data carrier includes essential features of one or more embodiments of the method and is at the same time a key for practical implementation of the method.

Other features which are considered as characteristic for the invention are set forth in the appended claims.

Although the invention is illustrated and described herein as embodied in a method and an apparatus for determining a cell density of a honeycomb body, in particular for an exhaust gas catalytic converter, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 1 is a diagrammatic, partly perspective and partly elevational view of a configuration for carrying out the method with a honeycomb body, an optical instrument and a computer;

FIG. 2 is an enlarged, sectional view of a part of a cell structure with a frame in the form of a circular ring; and FIG. 3 is an elevational view of an image recording apparatus with a matrix camera, an internal lamp and an external light shielding device.

DESCRIPTION OF THE PREFERRED EMBODIMETNS

Referring now to the figures of the drawings in detail and first, particularly, to FIG. 1 thereof, there is seen a configuration having a honeycomb body 1 with a plurality of passages 3 which are open-ended at an end 2 of the honeycomb body 1. A cell structure 4 which is visible at the end 2 has cells 5 that are bordered by cell edges 11. An optical instrument 9 is disposed above the end 2 of the honeycomb body 1. The optical instrument 9 is connected to a computer 8 by way of a line 22 for the purpose of digital image processing. Results of an image processing operation can be displayed on a display screen 7.

A preferred embodiment of the method according to the invention will be described below with reference to FIG. 2. A frame 10 in the form of a circular ring is fitted onto an approximately flat end of a honeycomb body to be checked. The frame 10 is formed of a material which is a good reflector of light and it has inner and outer circular diameters which are known. An image of a portion of the cell structure 4 which is formed by smooth sheet layers 20 and corrugated sheet layers 21 is recorded so that the entire ring-shaped frame 10 and its interior are detected. The image is broken down into digital pixels, with a grey value being allocated to each pixel. The cell edges 11 and the ring-shaped frame 10 are detected through the use of their grey values which are below a threshold value. A pixel represents in part a light cell edge 11 and in part a dark region which is bordered by the light cell edge 11. Therefore, under some circumstances, a mean grey value which is associated therewith is still beneath the threshold value. In that way the cell edges 11 appear to be of increased width. In the image processing operation the increase in width is corrected by thinning out the cell edges 11.

Counting out the pixels in two different, mutually perpendicular directions and comparing with the predetermined outside diameter of the ring-shaped frame 10 makes it possible to determine image scales for the two directions, for example in pixels per inch. A check is made to ascertain whether or not there is an unacceptably high degree of image distortion, which points to the optical instrument being in a tilted position. The operation of determining the area-related cell density may possibly be broken off.

Otherwise, the ring-shaped frame 10 is separated from its interior in the image processing operation and only the interior is subjected to further processing, that is to say the grey values of the pixels, which are associated with the ring-shaped frame 10, are set to a defined value, for example 100. Since generally not all of the cells in the interior of the ring-shaped frame 10 are cells 6 with respect to which a complete image has been produced, an image is formed with branching phenomena at the edge. The branching configurations are detected and also removed. What remains is an image with a cohesive region of cells 6 with respect to which a complete image is formed and which are then counted. Cell cross-sectional areas are also determined and summed in relation to a reference area. A check is performed to ascertain whether or not there are implausibly large or small cell cross-sectional areas. If there is an excessively small cell cross-sectional area it is assumed that one cell too many was incorrectly recognized and the error is corrected by reducing the number of cells by 1. In the case of a cell cross-sectional area which is substantially larger than the average cell cross-sectional area, the number of cells is increased in accordance with the quotient of the cell cross-sectional area and the average cell cross-sectional area. Finally, the area-related cell density is ascertained by relating the corrected number of cells to the sum of the cell cross-sectional areas.

The cell structure shown in FIG. 2 is that of a honeycomb body with alternate smooth and corrugated sheet layers. The described method is particularly advantageous since double or multiple cells which are to be counted as two or more cells occur in particular in the case of such honeycomb bodies due to connections between the layers which were intended but which have not been produced.

FIG. 3 shows a preferred embodiment of an image recording apparatus for carrying out the method according to the invention. A tube 19 which is held by a tube holder 17 contains a matrix camera 12 that is connected to the tube by way of a camera holder 18, an objective 16 and a circular slit lamp 13. An external light shielding device 14 which is disposed at a lower end of the tube 19 conically tapers towards an object opening 15 having a flat edge. The image recording apparatus can be displaced, for example through the use of a displacement device connected to the tube holder 17, to the end of a honeycomb body which is positioned beneath the apparatus. The displacement causes the periphery of the edge of the object opening 15 to bear against the end of the honeycomb body.

The present invention automates the procedure for determining an area-related cell density of a cell structure of a honeycomb body. The cell density can be determined quickly and precisely, particularly when using computer-aided image processing. In that way production errors can be rapidly detected and expense can be saved in that manner.

We claim:

1. A method of automatically determining an area-related cell density of a cell structure of a honeycomb body including a multiplicity of passages having open ends at an end of the honeycomb body at which the cell structure is visible, the method which comprises:

recording an image of at least a portion of the cell structure, with an optical instrument, the image having a known image scale;

processing the image by establishing a number of cells by counting cells and calculating the cell density by relating the number of cells to a reference area established with the aid of the image scale; and only counting cells for which a complete image is produced, establishing cell cross-sectional areas of the individual cells with the image scale, and equating the sum of the individual cell cross-sectional areas to the reference area.

2. The method according to claim 1, which comprises forming a continuous region of the cell structure with the counted cells.

3. The method according to claim 1, which comprises calculating an area average of the cell cross-sectional areas, establishing an area tolerance range, and not contributing a cell to the number of cells if the cell cross-sectional area of the cell falls below the area tolerance range.

4. The method according to claim 1, which comprises calculating an area average of the cell cross-sectional areas, establishing an area tolerance range, and contributing a cell to the number of cells at least two times if the cell cross-sectional area of the cell exceeds the area tolerance range.

5. The method according to claim 1, which comprises illuminating the end of the honeycomb body for reflecting light from cell edges in the direction of the optical instrument.

6. The method according to claim 1, which comprises processing the image with a computer program receiving predeterminable parameter values by suitable value allocations.

7. The method according to claim 6, which comprises representing a configuration of counted cells in two-dimensional form, as a result of the image processing step.

8. The method according to claim 7, which comprises carrying out the step of representing the configuration of counted cells on a display screen.

9. The method according to claim 7, which comprises including uncounted cells in the configuration and emphasizing the counted cells optically in comparison with the uncounted cells.

10. The method according to claim 9, which comprises carrying out the step of emphasizing the counted cells in color.

11. The method according to claim 1, which comprises processing the image with a computer program receiving a scale value by suitable value allocations.

12. The method according to claim 11, which comprises representing a configuration of counted cells in two-dimensional form, as a result of the image processing step.

13. The method according to claim 12, which comprises carrying out the step of representing the configuration of counted cells on a display screen.

14. The method according to claim 12, which comprises including uncounted cells in the configuration and emphasizing the counted cells optically in comparison with the uncounted cells.

15. The method according to claim 14, which comprises carrying out the step of emphasizing the counted cells in color.

16. A method of automatically determining an area-related cell density of a cell structure of a honeycomb body including a multiplicity of passages having open ends at an end of the honeycomb body at which the cell structure is visible, the method which comprises:

recording an image of at least a portion of the cell structure, with an optical instrument, the image having a known image scale;

processing the image by establishing a number of cells by counting cells and calculating the cell density by relating the number of cells to a reference area established with the aid of the image scale; and immovably mounting a scale object of known dimensions to the end of the honeycomb body, and at least also partially recording the scale object in the image for establishing a scale with which the image scale is formed.

17. The method according to claim 16, which comprises gluing the scale object to the end of the honeycomb body.

18. The method according to claim 16, wherein the scale object has a dimension along an extent of the cell structure which is substantially greater than its dimension perpendicular to the extent of the cell structure.

19. The method according to claim 18, which comprises framing a region of cells with the scale object in the form of a frame, completely recording the framed region and at least an inner frame edge in the image, and counting exclusively cells from the framed region.

20. The method according to claim 18, which comprises framing a region of cells with the scale object in the form of a circular ring frame, completely recording the framed region, an inner frame edge and an outer frame edge in the image, and counting exclusively cells from the framed region.

21. A method of automatically determining an area-related cell density of a cell structure of a honeycomb body including a multiplicity of passages having open ends at an end of the honeycomb body at which the cell structure is visible, the method which comprises:

recording an image of at least a portion of the cell structure, with an optical instrument, the image having a known image scale;

processing the image by establishing a number of cells by counting cells and calculating the cell density by relating the number of cells to a reference area established with the aid of the image scale;

illuminating the end of the honeycomb body for reflecting light from cell edges in the direction of the optical instrument; and forming a brightness average value over at least a part of the image, establishing a brightness threshold value above the brightness average value, and inferring a position of the cell edges from a position of image regions having a brightness above the brightness threshold value.

22. An apparatus for automatically determining an area-related cell density of a cell structure of a honeycomb body, the apparatus comprising:

a scale object having known dimensions for establishing a reference area, said scale object framing a region of cells at an end of the honeycomb body;

an optical instrument having a matrix camera for recording an image of the honeycomb body and at least partially of the image object, including:
a peripherally closed external light shielding device having an object opening; and
an internal lamp for illuminating the end of the honeycomb body, said internal lamp emitting light passing outwardly from said external light shielding device through said object opening upon said internal lamp being turned on; and a data processing installation connected to said optical instrument for ascertaining a number of cells by counting cells and for calculating a cell density by relating the number of cells to said reference area.

23. The apparatus according to claim 22, wherein said internal lamp is a circular slit lamp, and said object opening has a flat edge.

24. The apparatus according to claim 22, wherein said object opening has an edge bearing against the end of the honeycomb body.

25. The apparatus according to claim 24, wherein said edge of said object opening is peripheral.

* * * * *